US010395964B2

(12) United States Patent
Busche et al.

(10) Patent No.: US 10,395,964 B2
(45) Date of Patent: Aug. 27, 2019

(54) APPARATUS AND METHOD FOR MEASUREMENT OF THE THERMAL PERFORMANCE OF AN ELECTROSTATIC WAFER CHUCK

(71) Applicant: APPLIED MATERIALS, INC., Santa Clara, CA (US)

(72) Inventors: Matthew J. Busche, Santa Clara, CA (US); Vijay D. Parkhe, San Jose, CA (US); Michael R. Rice, Pleasanton, CA (US)

(73) Assignee: Applied Materials, Inc., Santa Clara, CA (US)

( * ) Notice: Subject to any disclaimer, the term of this patent is extended or adjusted under 35 U.S.C. 154(b) by 114 days.

(21) Appl. No.: 15/792,596

(22) Filed: Oct. 24, 2017

(65) Prior Publication Data
US 2018/0047607 A1     Feb. 15, 2018

Related U.S. Application Data

(62) Division of application No. 14/179,339, filed on Feb. 12, 2014, now Pat. No. 9,831,111.

(51) Int. Cl.
*H01L 21/68* (2006.01)
*H01L 21/683* (2006.01)
*H01L 21/67* (2006.01)
*G01N 21/95* (2006.01)

(52) U.S. Cl.
CPC .... *H01L 21/6833* (2013.01); *H01L 21/67103* (2013.01); *H01L 21/67248* (2013.01); *G01N 21/9501* (2013.01)

(58) Field of Classification Search
CPC .................................................. H01L 21/6833
USPC .......................................................... 438/716
See application file for complete search history.

(56) References Cited

U.S. PATENT DOCUMENTS

| | | |
|---|---|---|
| 4,854,724 A | 8/1989 | Adams et al. |
| 4,979,134 A | 12/1990 | Arima et al. |
| 5,098,198 A | 3/1992 | Nulman et al. |
| 5,417,494 A | 5/1995 | Kempa et al. |
| 5,889,258 A | 3/1999 | Lubomirski et al. |
| 6,479,801 B1 | 11/2002 | Shigeoka et al. |
| 6,876,442 B2 | 4/2005 | Vatus et al. |
| 2002/0042206 A1 | 4/2002 | Masuda et al. |
| 2003/0199283 A1 | 10/2003 | Busch |
| 2007/0062439 A1 | 3/2007 | Wada et al. |
| 2008/0274604 A1 | 11/2008 | Sanchez et al. |
| 2009/0093135 A1 | 4/2009 | Matsushita et al. |
| 2009/0316749 A1 | 12/2009 | Davis |

(Continued)

OTHER PUBLICATIONS

International Search Report and Written Opinion from PCT/US2015/014315 dated May 7, 2015, 14 pgs.

(Continued)

*Primary Examiner* — Roberts P Culbert
(74) *Attorney, Agent, or Firm* — Schwabe, Williamson & Wyatt, P.C.

(57) ABSTRACT

An apparatus and method are described for measuring the thermal performance of a wafer chuck, such as an electrostatic chuck. In one example, the apparatus ha a chamber, a base to support a wafer chuck in the chamber, a heater to heat the chuck, a window through the exterior of the chamber, and an infrared imaging system to measure the temperature of the chuck while the chuck is heated.

7 Claims, 7 Drawing Sheets

(56) References Cited

U.S. PATENT DOCUMENTS

| | | |
|---|---|---|
| 2010/0232470 A1 | 9/2010 | Timans |
| 2011/0295539 A1* | 12/2011 | Tsai ................. H01L 21/67248 |
| | | 702/99 |
| 2012/0201267 A1 | 8/2012 | Patalay |
| 2012/0288970 A1 | 11/2012 | Hashimoto et al. |
| 2013/0248504 A1 | 9/2013 | Kusuda |
| 2015/0023385 A1 | 1/2015 | Patalay et al. |

OTHER PUBLICATIONS

International Preliminary Report on Patentability from PCT/US2015/014315 dated Aug. 25, 2016, 10 pgs.

Non-Final Office Action from U.S. Appl. No. 14/179,339 dated Nov. 14, 2016, 10 pgs.

Final Office Action from U.S. Appl. No. 14/179,339 dated Apr. 25, 2017, 8 pgs.

* cited by examiner

APPARATUS AND METHOD FOR MEASUREMENT OF THE THERMAL PERFORMANCE OF AN ELECTROSTATIC WAFER CHUCK

CROSS-REFERENCE TO RELATED APPLICATIONS

This application is a divisional application of U.S. patent application Ser. No. 14/179,339, filed on Feb. 12, 2014, the entire contents of which are hereby incorporated by reference herein.

TECHNICAL FIELD

Embodiments of the present invention relate to the microelectronics manufacturing industry and more particularly to temperature controlled chucks for supporting a workpiece during plasma processing.

BACKGROUND

In the manufacture of semiconductor chips a silicon wafer or other substrate is exposed to a variety of different processes in different processing chambers. The chambers may expose the wafer to plasmas, chemical vapors, metals, laser etching, and various deposition and acid etching processes in order to form circuitry and other structures on the wafer. During these processes, the silicon wafer may be held in place by an electrostatic chuck (ESC). The chuck holds the wafer by generating an electrostatic field to clamp the back side of the wafer to a flat surface or puck surface of the chuck.

As fabrication techniques for plasma processing equipment advance, such as those designed to perform plasma etching of microelectronic devices and the like, the temperature of the wafer during processing becomes more important.

ESCs have been designed for thermal uniformity across the surface of the substrate, sometimes called a workpiece. ESCs use liquid cooling to absorb the plasma power heat and remove it from the chuck. An ESC may also include independently controlled heaters in multiple zones. This allows for a wider process window under different process and plasma conditions. Individual heater zones in the radial direction can create various radial temperature profiles which compensate for other etch process radial non-uniformities.

In semi-conductor etch processing, the temperature of a wafer during processing influences the rate at which structures on the wafer are etched. Other processes may also have a temperature dependence. This temperature influence is present, for example, in conductor etch applications in which very precise wafer temperature control helps to obtain a uniform etch rate. A more precise thermal performance allows for more precisely formed structures on the wafer. Uniform etch rates across the wafer allow smaller structures to be formed on the wafer. Thermal performance or temperature measurement and control is therefore a factor in reducing the size of transistors and other structures on a silicon chip.

SUMMARY

An apparatus and method are described for measuring the thermal performance of a wafer chuck, such as an electrostatic chuck. In one example, the apparatus ha a chamber, a base to support a wafer chuck in the chamber, a heater to heat the chuck, a window through the exterior of the chamber, and an infrared imaging system to measure the temperature of the chuck while the chuck is heated.

BRIEF DESCRIPTION OF THE DRAWINGS

Embodiments of the present invention are illustrated by way of example, and not limitation, in the figures of the accompanying drawings in which.

DETAILED DESCRIPTION

Figure 1:
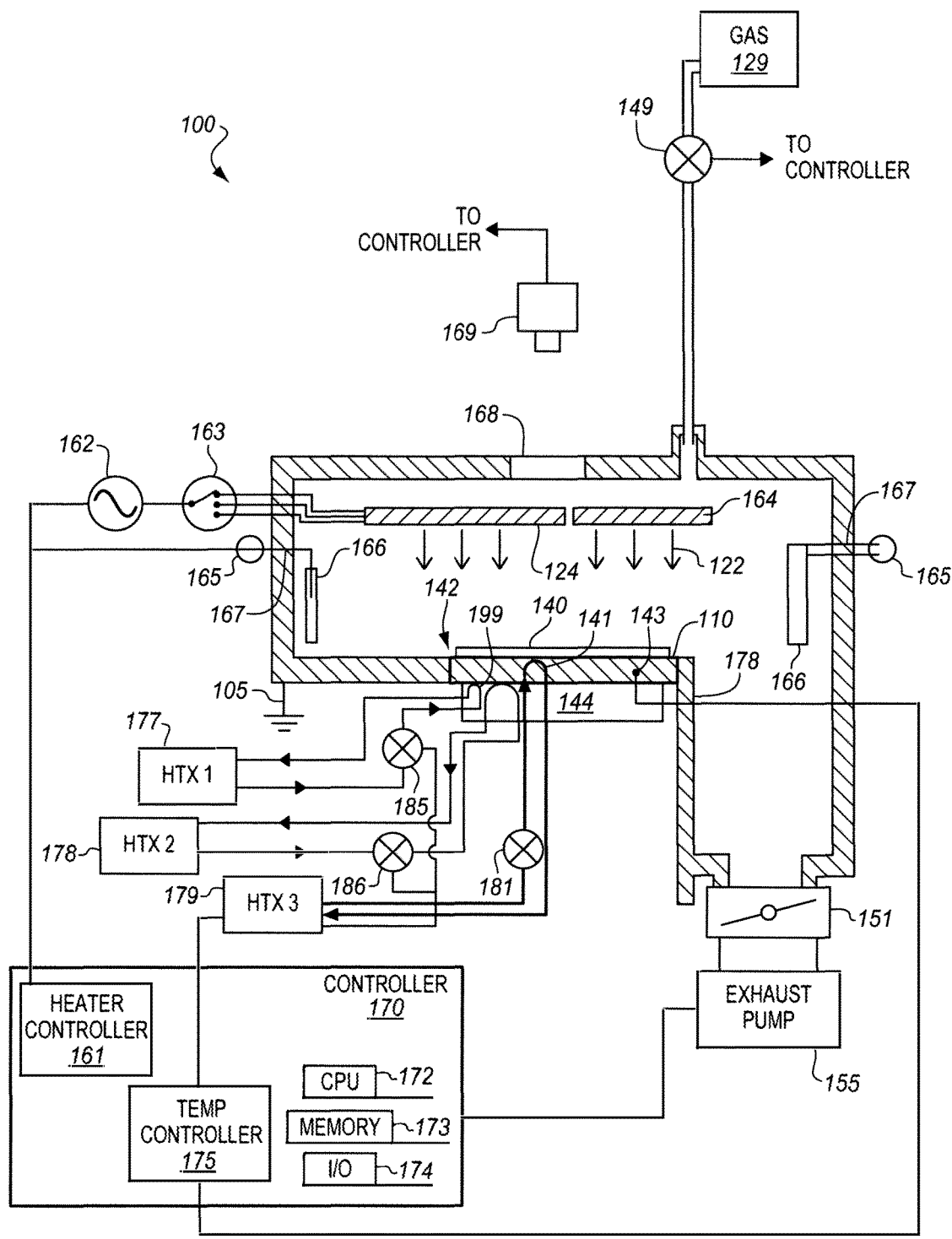
FIG. 1 is a schematic of a thermal performance measurement system including a chuck assembly in accordance with an embodiment of the present invention.

In the following description, numerous details are set forth, however, it will be apparent to one skilled in the art, that the present invention may be practiced without these specific details. In some instances, well-known methods and devices are shown in block diagram form, rather than in detail, to avoid obscuring the present invention. Reference throughout this specification to "an embodiment" or "one embodiment" means that a particular feature, structure, function, or characteristic described in connection with the embodiment is included in at least one embodiment of the invention. Thus, the appearances of the phrase "in an embodiment" or "in one embodiment" in various places throughout this specification are not necessarily referring to the same embodiment of the invention. Furthermore, the particular features, structures, functions, or characteristics may be combined in any suitable manner in one or more embodiments. For example, a first embodiment may be combined with a second embodiment anywhere the particular features, structures, functions, or characteristics associated with the two embodiments are not mutually exclusive.

As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items.

The terms "coupled" and "connected," along with their derivatives, may be used herein to describe functional or structural relationships between components. It should be understood that these terms are not intended as synonyms for each other. Rather, in particular embodiments, "connected" may be used to indicate that two or more elements are in direct physical, optical, or electrical contact with each other. "Coupled" my be used to indicate that two or more elements are in either direct or indirect (with other intervening elements between them) physical, optical, or electrical contact with each other, and/or that the two or more elements co-operate or interact with each other (e.g., as in a cause an effect relationship).

The terms "over," "under," "between," and "on" as used herein refer to a relative position of one component or material layer with respect to other components or layers where such physical relationships are noteworthy. For example in the context of material layers, one layer disposed over or under another layer may be directly in contact with the other layer or may have one or more intervening layers. Moreover, one layer disposed between two layers may be directly in contact with the two layers or may have one or more intervening layers. In contrast, a first layer "on" a second layer is in direct contact with that second layer. Similar distinctions are to be made in the context of component assemblies.

The temperature uniformity across the surface of an ESC has been improved with improved cooling plate and heater designs and improvements in bonding the cooling plate to the puck that holds the workpiece. However, these designs and processes are still subject to manufacturing variations, which can lead to significant thermal non-uniformity. For some implementations, a spatial temperature variation of less than +/−0.3° C. across the wafer is desired.

FIG. 1 is a schematic of an electrostatic chuck testing platform 100 that is able to mimic the thermal environment of a plasma etch system. The test system 100 includes a grounded chamber 105. Recharge gases, either ambient air, nitrogen or other gases are supplied from gas source(s) 129 connected to the chamber through a mass flow controller 149 to the interior of the chamber 105. Chamber 105 is evacuated via an exhaust valve 151 connected to a high capacity vacuum pump stack 155.

A wafer 110 may be used to further characterize the performance of the chuck. If so the wafer may be loaded into the chamber and clamped to the chuck assembly 142 inside the chamber. The workpiece 110, such as a semiconductor wafer, may be any wafer, substrate, or other material employed in the semi-conductor processing art and the present invention is not limited in this respect. The workpiece 110 is disposed on a top surface of a dielectric layer 143 or puck of the chuck assembly that is disposed over a cooling base assembly 144 of the chuck assembly. A clamp electrode (not shown) is embedded in the dielectric layer 143. In particular embodiments, the chuck assembly 142 may include different heater zones, such as a center zone 141 and edge zones 199, each zone 141, 199 may be independently controllable to the same or to different temperature set points. The chuck assembly 144 includes a base to carry the chuck including the heaters, cooling system, and the puck. A variety of different chucks may be placed on the base of the chuck assembly for testing purposes.

A system controller 170 is coupled to a variety of different systems to control a chuck testing process in the chamber. The controller 170 may include a temperature controller 175 to execute temperature control algorithms (e.g., temperature feedback control) and may be either software or hardware or a combination of both software and hardware. The system controller 170 also includes a central processing unit 172, memory 173 and input/output interface 174. The temperature controller 175 is to output control signals affecting the rate of heat transfer between the chuck assembly 142 and a heat source and/or heat sink external to the chamber 105 for the various heater zones 141, 199.

In embodiments, in addition to the different heaters, there may be different coolant temperature zones. The coolant zones may include separate, independently controlled heat transfer fluid loops with separate flow control that is controlled based on a zone-specific temperature feedback loop. In the example embodiment, the temperature controller 175 is coupled to a first heat exchanger (HTX)/chiller 177 and may further be coupled to a second HTX/chiller 178 and a third HTX/chiller 179. The flow rate of the heat transfer fluid or coolant through conduits in the chuck assembly 142 may also be controlled by the heat exchangers.

One or more valves 185, 186 (or other flow control devices) between the heat exchanger/chillers 177, 178, 179 and fluid conduits in the chuck assembly 142 may be controlled by the temperature controller 175 to independently control a rate of flow of the heat transfer fluid to each of the different cooling zones. The heat transfer fluid may be a liquid, such as, but not limited to deionized water/ethylene glycol, a fluorinated coolant such as Fluorinert® from 3M or Galden® from Solvay Solexis, Inc. or any other suitable dielectric fluids such as those containing perfluorinated inert polyethers. While the present description describes the ESC in the context of a plasma processing chamber, the ESC described herein may be used in a variety of different chambers and for a variety of different processes.

The controller also has a heater controller 161 that is coupled to a current source 162 to drive a heater 164 inside the chamber. The current may be coupled through a switch matrix 163 to independently control different zones of the heater. The heater applies heat to the chuck through thermal radiation in order to simulate heat that might be generated by a plasma source in an etch chamber. The heater controller is also coupled to an array of shutters 166. The shutters are hinged at one end and driven by shafts 167 or electromagnetic coupling by exterior rotary motors 165. The shutters open and close to allow radiant heat 122 from the heater to be blocked during imaging or passed to simulate a plasma heat load. The quick cycling of the heat by the shutters further simulates the environment inside an etch chamber.

The test system also has a window 168 at the top of the chamber. The window allows a thermal imaging camera 169 to observe the chuck 142 and the wafer 140, if any, through a central hole 124 in the heater the temperature profile across the surface of the chuck or wafer can be observed and measured at different chamber temperatures. Using this apparatus the quality and the performance of the chuck can be determined.

Figure 2:
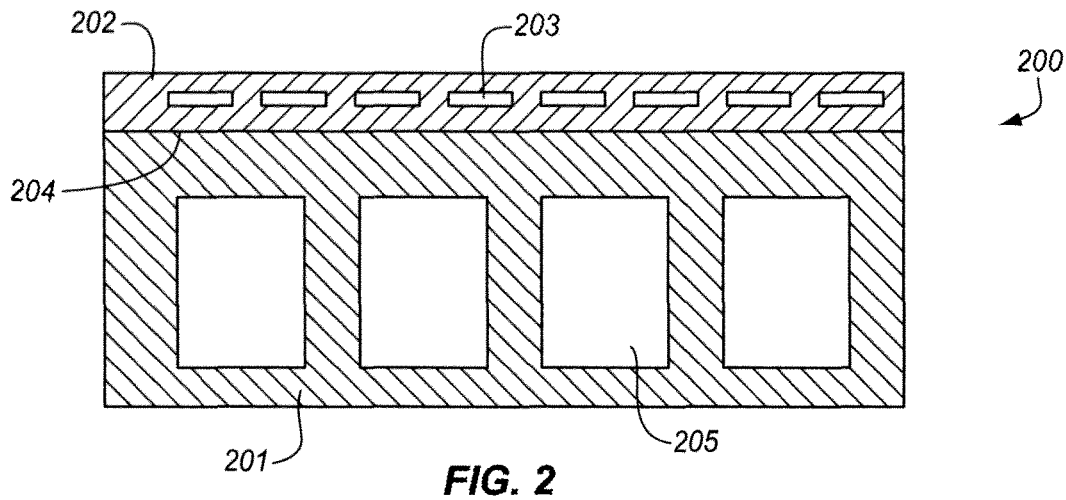
FIG. 2 is a simplified cross-sectional diagram of a portion of an electrostatic chuck in accordance with an embodiment of the invention.

FIG. 2 is a simplified cross-sectional diagram of a portion of an electrostatic chuck (ESC) 200. There are at least four components for regulating the temperature of the chuck surface and therefore the temperature of a wafer (not shown) on the chuck. A cooling plate 201, typically made from a thermally conducting metal serves as a heat sink. The cooling plate is bonded to a dielectric puck 202 with a high temperature adhesive 204 such as silicon. The puck is typically ceramic but may alternatively be made with other materials. Electrodes (not shown) are embedded within the puck to generate an electrostatic field with which to grip a workpiece, such as a silicon substrate. Resistive heater traces 203 are also embedded within the puck for temperature control.

The cooling plate 201 also includes channels 205 for coolant. Coolant is pumped through the channels to absorb heat from the cooling plate and pumped to a heat exchanger to cool the fluid which is then recirculated back to the cooling plate. The cooling plate absorbs heat from the embedded heaters and the workpiece through the ceramic plate. The temperature uniformity depends on the quality of the ceramic puck 202 the elastomer bound 204 and the cooling plate channels 205. It also depends on how well heat is transferred from the workpiece to the ceramic puck. All of these factors are subject to variations in manufacture and use.

Figure 3:
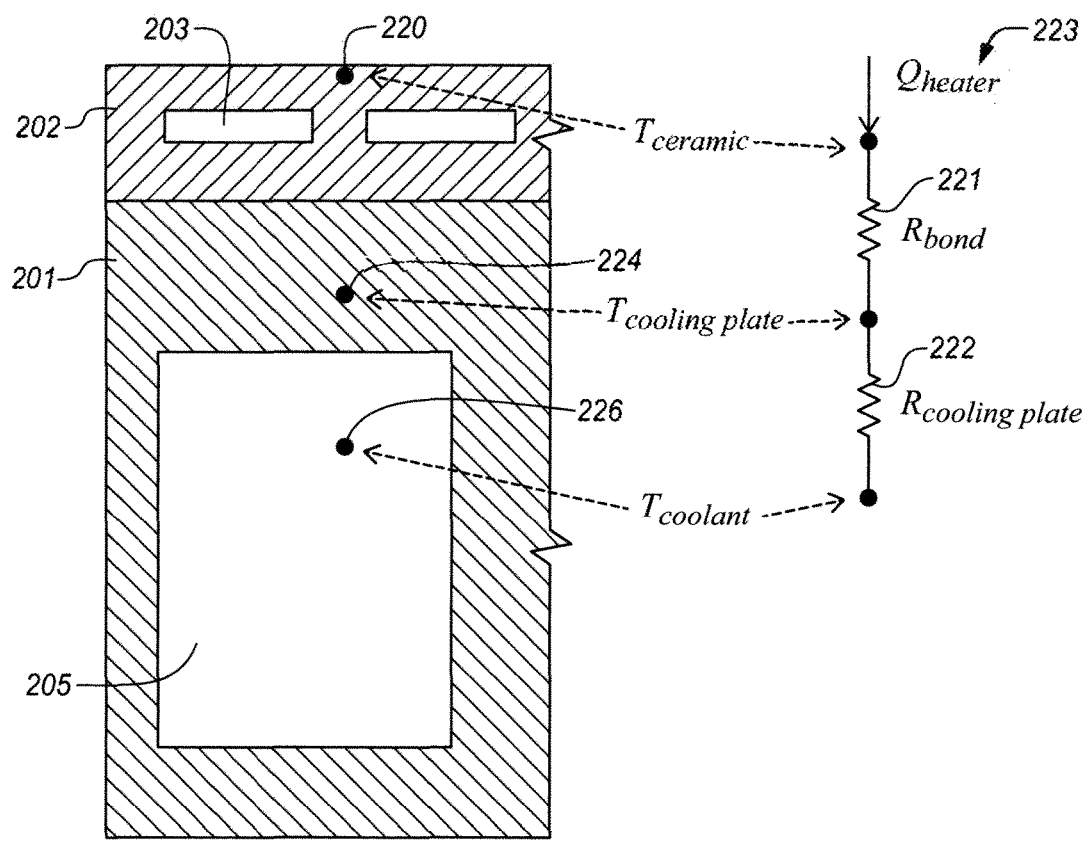
FIG. 3 is a simplified cross-sectional diagram of a model of ESC temperature and thermal conduction for an electrostatic chuck in accordance with an embodiment of the invention.

FIG. 3 is a simplified one dimensional diagram of a model of ESC temperature and thermal conduction. The diagram is presented using the same components and reference numbers as in FIG. 2 however only a portion of the FIG. 2 diagram is shown for reference. In this model the ceramic temperature T ceramic at a given location 220 is determined in part by the thermal resistances of the cooling plate (R cooling plate) 222 and the bond (R bond) 221. Heat is provided by the heater power (Q heater) 223 and removed by the cooling plate (T cooling plate 224) and by the coolant (T coolant 226). The thermal resistance is presented for purposes of explanation. The components of FIG. 3 may be described as follows:

Q heater 223: The heater power at a given point on the ESC surface is determined by the number of heater traces in the area and the electrical resistance of those heater traces. When the chuck is in use, heat is also applied by the plasma. For Testing purposes, the heaters May be used to simulate plasma processing or any other high temperature processing or a different external or internal heat source may be used. If the heater traces produce sufficient heating, then the heater traces may be used. Rather than generating temperatures similar to those used for plasma processing, the heater traces may be used simply to generate a measurable heat flow from the ceramic puck 202 to the other components.

R bond 221: The resistance of the bond is determined by the thermal conductivity of the bond material, the bond thickness, and the quality of the bond connection both to the cooling plate and to the ceramic puck.

T cooling plate 224: The temperature of the cooling plate is largely controlled by the conduction of heat from the ceramic puck through the bond and into the coolant. The flow of heat into the coolant at any one location 224 of the cooling plate is affected by at least two factors: 1) the coolant temperature increases as it travels through the cooling plate so that the coolant at different locations of the cooling plate will be at different temperatures and 2) feedthrus and other features of the cooling plate constrain where the cooling channels can be placed in the cooling plate so that some locations have more coolant flow then others.

R cooling plate 222: The thermal resistance of the cooling plate is a combined function of the local fluid heat transfer coefficient, the geometry of the cooling plate, and the thermal conductivity of the cooling plate.

T coolant 226: The temperature of the coolant entering the cooling plate may be carefully controlled by a heat exchanger or chiller. However, as the coolant travels through the cooling plate, its temperature increases. In a typical application, the coolant temperature may rise by up to 10° C. So the local coolant temperature at a given point on the ESC varies greatly.

T ceramic: The temperature of the ESC ceramic at any one particular location 220 may be estimated using the relationship:

$$T\ ceramic = Q\ heater\ R\ bond + Q\ heater\ R\ cooling\ plate + T\ coolant.$$

This shows that to achieve a uniform temperature across the ceramic puck, R cooling plate may be adjusted at each location to compensate for variation of R bond, Q heater, and T coolant. Alternatively, another way to achieve the most uniform ceramic temperature possible is to design the heater traces (and hence Q heater) to compensate for the spatial variations of the cooling plate temperature. In other words Q heater is adjusted based on variations in R cooling plate and T coolant.

In an ideal ESC design, the heater watt density will be matched to perfectly compensate for variations in the cooling plate temperature. The bond thickness is uniform. As a result, the ceramic temperature is uniform in every dimension. In any real manufactured ESC, the ceramic temperature is non-uniform due to several factors. First, the design of the heater traces may not be perfect. As a result an ideally uniform watt density is difficult to achieve. Second, the heater traces are manufactured or created using a screen printing process. Printing error causes the actual watt density to deviate still further from the imperfect values that were designed for the traces. Third, the bond thickness of the adhesive varies. As a result, a typical manufactured ESC does not have perfectly uniform bond heat resistance.

Figure 4:
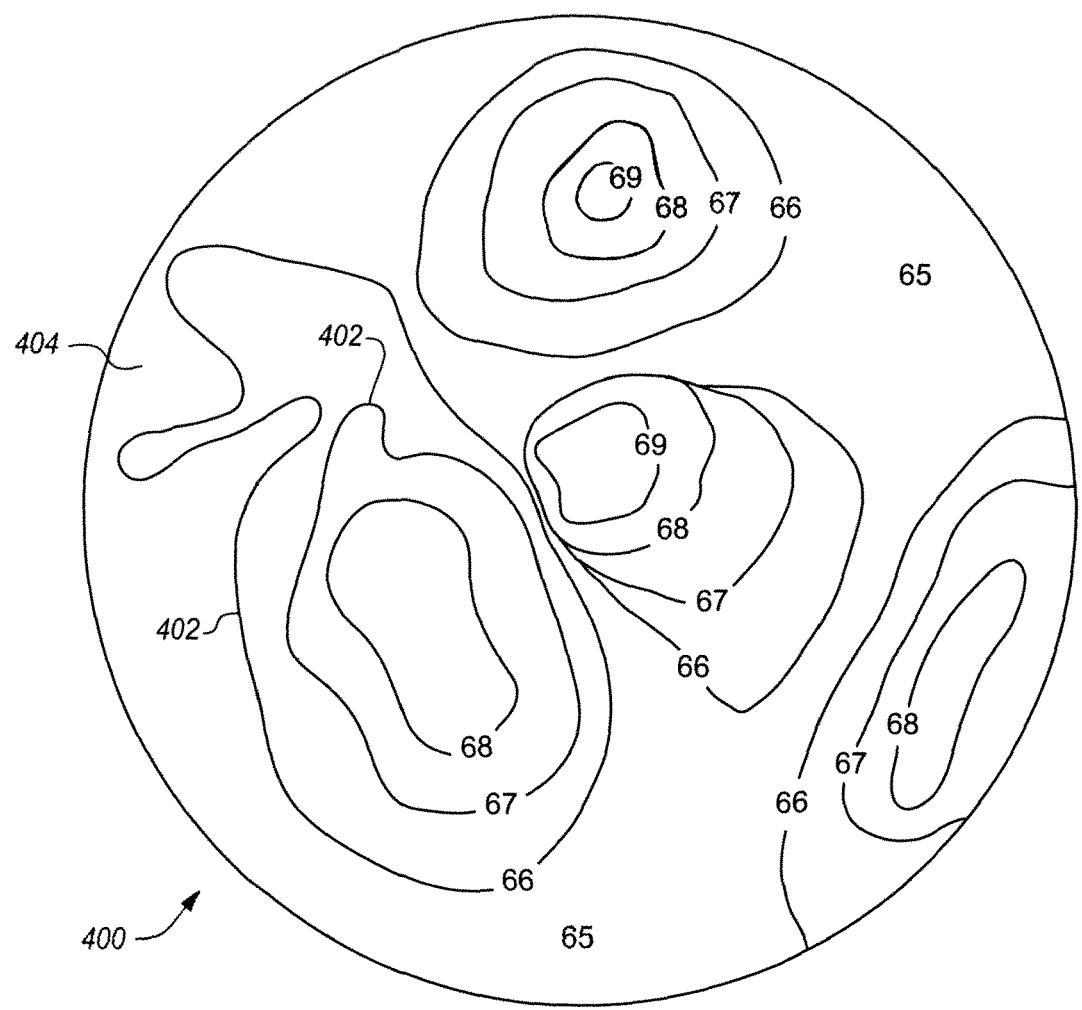
FIG. 4 is a diagram of a top elevation contour line graph of the temperature of a wafer in a processing chamber.

FIG. 4 is a diagram of a top elevation graph 400 of the temperature of a wafer 404 on an ESC. This graph shows surface temperature as a function of position on the wafer using contour lines 402. Such a diagram may be generated based on a measurement of an actual ESC as it is heated by the conductive traces and cooled by coolant flowing through the channels of the cooling base. Such measurements may be made by heating a wafer and then measuring the temperature at different positions using an infrared camera. As shown, the temperature values shown on the surface temperature contour lines vary in a pattern that is related to manufacturing and design features of the ESC. Contour lines are shown only for integer temperature values in order to simplify the diagram. For an actual measurement, much higher accuracy, for example tenths of a degree may be desired.

In order to even out the temperatures and obtain a more uniform temperature across the ESC, external adjustments can be made to the coolant flow within the ESC. In one example, the cooling plate contains many (e.g. 50+) small flow adjustable orifices. These orifices may be adjusted by mechanically changing their size or by replacing an insert, such as a sleeved tube. Adjustments to the coolant flow through the orifices may be based on a one-time calibration using an infra-red camera. The calibration can compensate for manufacturing defects in the ESC and drastically improve the thermal performance characteristics of the cooling plate. The calibration process may use the measurements to adjust each orifice based on feedback from an infra-red camera. The cooling plate may be measured and the orifices adjusted in an iterative process until the desired heat distribution is obtained.

Figure 5:
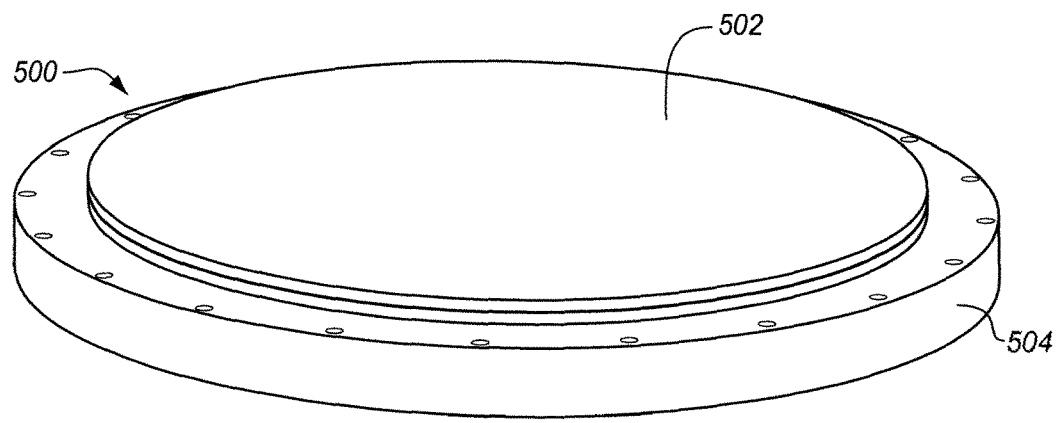
FIG. 5 is an isometric view of an electrostatic chuck in accordance with an embodiment of the invention.

FIG. 5 is an isometric view of an ESC 500 showing a ceramic puck 502 over a cooling plate 504. The diagram is simplified and does not include electrical, coolant and control connections. The diagram also does not show a variety of different "feedthru" holes in the ceramic puck. These holes are required to accommodate gas outlets, temperature probes, and wafer lift pins.

Figure 6:
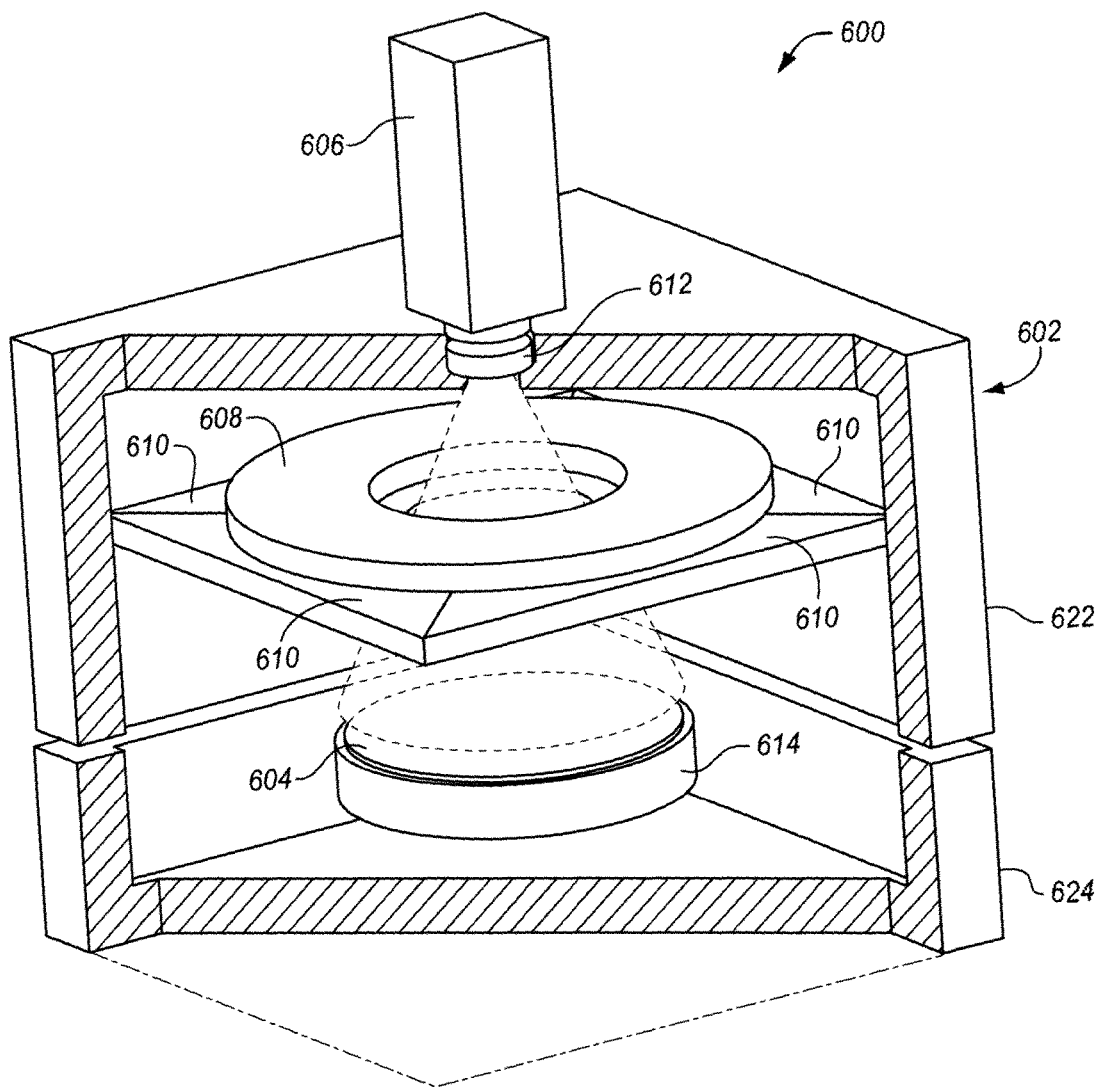
FIG. 6 is an isometric diagram partially cut away of a thermal performance measurement chamber with shutters closed in accordance with an embodiment of the invention.

FIG. 6 is an isometric view, partially cut-away of a system that is adapted particularly for measuring the thermal performance of a chuck, such as the ESC of FIG. 5. The system has a vacuum chamber 602 for holding the chuck 604 on a suitable base 614. The base holds the chuck above the bottom of the chamber and provides an additional desired support and equipment. It may also provide heating, and cooling, depending on the particular implementation. A heater 608 inside the chamber is used to heat the chuck. Shutters 610, between the heater and the chuck, control when heat is applied to the chuck. A germanium window 612 through the exterior wall of the vacuum chamber allows an infrared camera 606 to measure the chuck temperature based on infrared radiation. These components are described in more detail below.

The vacuum chamber 602 is shown as a nearly cubic rectangular volume with six walls at right angles and all about the same size. If the vacuum chamber is used at or near standard atmospheric pressure (atm), with typical processing chamber vacuum, the pressure on the outside of the chamber will not be great. A rectangular chamber may easily be made to withstand many testing cycles. However, the chamber may be made in many different shapes and configurations. The chamber shape may be adapted to improve heat flow or internal heat reflection. The interior of the chamber may be coated or polished to reflect infrared radiation. In addition, the coating may be adapted to compensate for hot and cool areas in the chamber.

The test apparatus in the illustrated example includes upper 622 and lower 624 chamber halves. The two halves are connected by a hinge (not shown), and an o-ring (not shown) seals the two halves. The hinge allows the chamber to be opened to service components and to place the chuck that is to be tested. The chamber can then be closed and latched shut for another test.

A vacuum chamber is used for thermal testing for at least two reasons. First, the vacuum eliminates convective heat transfer. A partial or imperfect vacuum greatly reduces convective heat transfer. This allows the heat to be controlled more quickly. If the chuck is heated only or primarily by infrared emission from the heater, then the heat can be turned on or off quickly. Air in the chamber would absorb heat. If the heater were turned off, then the heated air would continue to heat the chuck. Similarly if the heat is turned on, then the air would absorb some of the heat. In both cases, the chuck responds more slowly to changes in the heater.

A second reason for using a vacuum chamber is that wafers can be chucked, either electrostatically or by differential vacuum. A differential vacuum makes it easier to hold and move wafers. A differential vacuum hold does not add heat.

A third reason is that many fabrication processes are performed in a vacuum. A vacuum chamber test will more closely resemble production conditions.

The particular environment inside the chamber may be modified as desired. For some thermal performance tests, a nitrogen or vapor environment may be preferred. In addition the quality or purity of the vacuum may be modified to suit particular testing purposes.

The chamber is cooled to reduce emission from other heat sources. Since the system is primarily intended to determine the thermal performance of the chuck, other heat sources within the chamber, including the chamber walls, may interfere with the heat measurements. Liquid cooling may be used to maintain a constant and uniform chamber temperature. This may be used to improve the accuracy of the thermal imaging.

The infrared camera 606 makes the temperature measurements of the chuck during tests. Any of a variety of different infrared cameras may be used. A commercially available camera such as a FLIR SC8000 with moderately high resolution (1024×1024), a fast frame rate (130 Hz) and high sensitivity (0.015° C.) allows the chuck to be more accurately characterized. The camera may be selected to meet the purpose of any particular testing system and testing purpose.

The germanium window 612 allows the camera to image the interior of the vacuum chamber from outside the vacuum chamber. For thermal imaging, the window is transparent to infrared radiation. While, the window may be made of a variety of different materials that are transparent in the infrared spectrum, germanium is readily available at reasonable cost.

The shutters 610 are formed from a set of plates that move between an open position and a closed position. When closed, the shutters block the thermal radiation from the heater from reaching the chuck. When open, the shutters allow the heater to heat the chuck. The shutters allow the thermal radiation load to be quickly turned on and off, mimicking the conditions in an etch process chamber. A heater element will almost always retain some residual heat slowing its response to on and off transitions. The shutters allow the heat to be blocked or allowed. The heater does not need to be switched the heat load on the chuck may be controlled through the shutters. In one embodiment, the shutters may be mounted on axles, with the axles driven externally by rotary vacuum feedthrus through the chamber walls.

Like the vacuum chamber walls, the shutters may be liquid cooled, in order to maintain a consistent background for thermal imaging. Since the shutters block most or all of the thermal radiation from the heater when closed, they are exposed to a significant heat load from the heater. This may be reduced by coating the shutters in a reflective material on the surfaces facing the heater. FIG. 6 shows the vacuum chamber with the chuck held in place near the bottom of the lower half of the chamber. The chuck is held apart from any wall of the chamber so that conductive heat transfer with other surfaces does not affect the camera image. The chuck is in the form of a wafer which is typically a round disk shape. The heater inside the chamber is mounted in the upper half of the chamber some distance from the chuck. In the illustrated example, the heater is an annulus above the chuck. This allows the camera to view the chuck through the central hole in the heater. The center of the chuck and the heater are aligned or close to aligned.

The shutters are directly below the heater, between the heater and the chuck. As a result, when the shutters are closed as shown in FIG. 6, there is a wall or thermal barrier horizontally across the interior of the chamber. The top of the chamber carrying the heater is walled off by the shutters from the lower part of the chamber that has the chuck.

Figure 7:
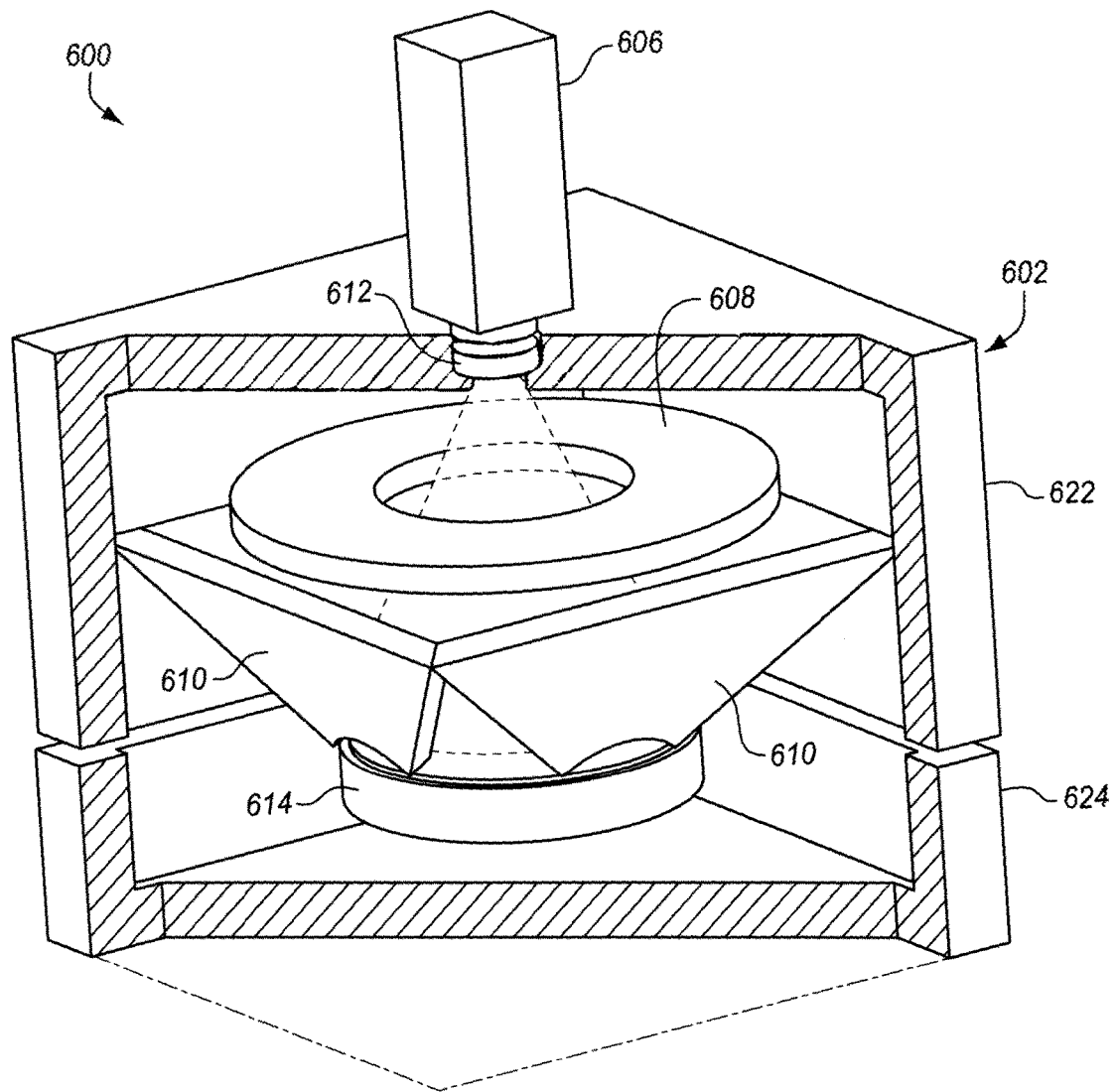
FIG. 7 is an isometric diagram partially cut away of a thermal performance measurement chamber with shutters open in accordance with an embodiment of the invention.

FIG. 7 shows the same chamber 602 with the same chuck 604 and heater 608. In this case, the shutters are open. In the open position the shutters are dropped down away from the heater and there is no barrier between the heater and the chuck. In this example, the shutters are the shape of four triangular leaves. One side of each triangle is placed against one of the four chamber side wall. The opposite corners move up and down from vertical against the side walls to horizontal where the corners meet in the middle of the chamber when the shutters are closed. Any of a variety of other shutter shapes may be used, depending on the particular implementation.

Referring again to FIG. 6, the heater is in the form of an annulus. The annular heater transfers a radiation heat load onto the ESC or wafer. The annulus provides for a uniform circular distribution of heat emission to coincide with the shape of the chuck. The central opening in the annulus allows the camera to view the chuck through the heater. The size of the hole in the middle of the heater may be determined based on the field of view of the camera lens, the relative distances of the camera, heater, and chuck and the size of the chuck. The heater may be made so that it has a diameter that is larger than the chuck and that the central opening is no larger than necessary to allow the camera to image the whole top surface of the chuck.

Figure 8:
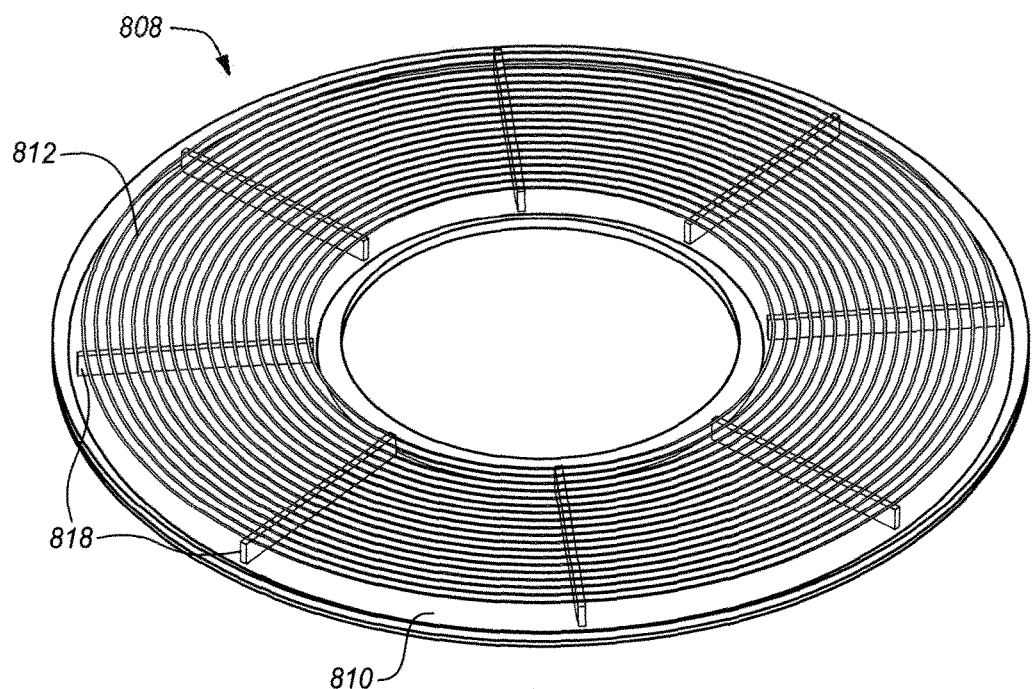
FIG. 8 is an isometric view of an annular heater with wire filaments in accordance with an embodiment of the invention.

The heater may be formed in any of a variety of different ways. In some embodiments, the heater may be formed from an array of heater filament wire as shown in FIG. 8. FIG. 8 is an isometric bottom view of a heater 808 that is formed based on a reflector dish 810. The reflector is formed from a rigid material that reflects or is coated to reflect infrared radiation of the type produced by the heater. An aluminum plate may be used. The dish may be polished to increase the reflectance of infrared radiation. Since the heater and the chuck are operating in a vacuum, the efficiency of the heater is improved by improving the transmission of heat toward the chuck. In the same way, the interior of the vacuum chamber may be made reflective to infrared radiation in order to enhance efficiency. This may be done by polishing, coating, painting, or in another way.

The reflector dish may be made from a single round plate of metal, composite, or other material with an appropriately sized hole through the middle. An array of radial standoffs 818 are mounted to the dish 810. The array of heater filaments 812 are mounted onto electrically insulating standoffs. The position and spacing of the filaments is set to achieve a uniform thermal radiation on the chuck. As a result, there may be more filaments toward the middle to compensate for the central opening.

The filaments are shown as being in concentric circles and resting on the standoffs. Alternatively, the filament may be a single spiral wound wire. In this example, the filaments act as resistive heaters that generate infrared radiation when a current is driven through the wire. The filament may also generate other light, heat, and other products, but the infrared radiation is the primary product of interest for this application. A wide variety of different filaments may be used that generate infrared radiation in response to a current. The filaments may be made of several isolated portions that are independently powered so that the heat in different parts of the heater can be adjusted independently.

Figure 9:
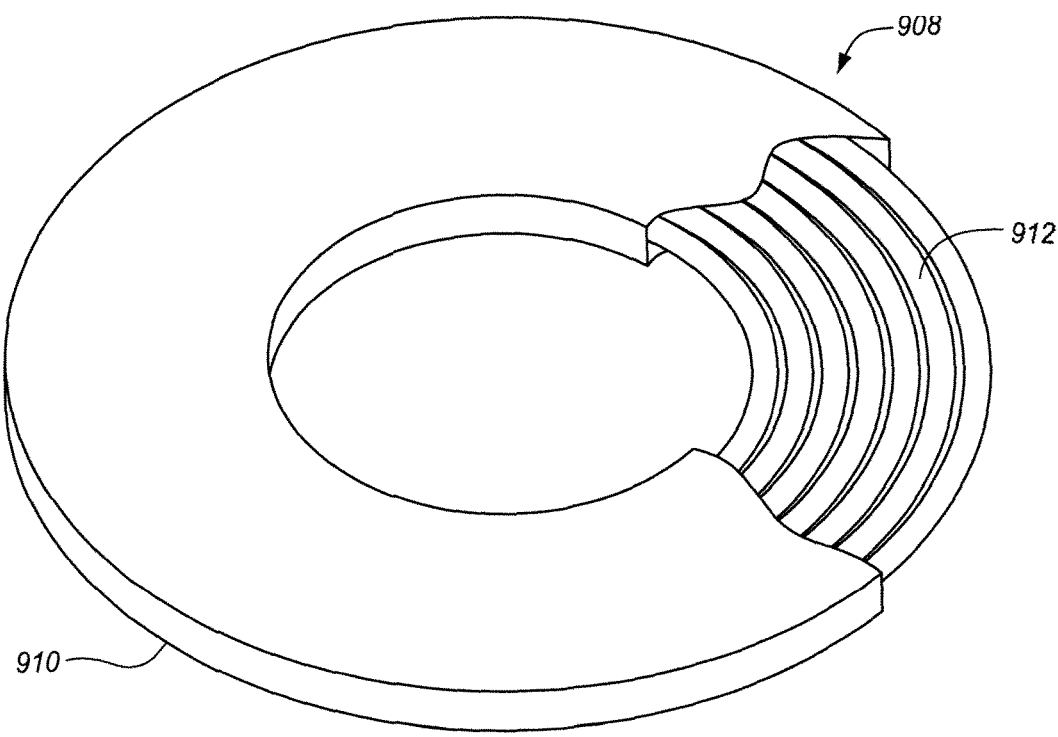
FIG. 9 is an isometric view of an annular case heater with concentric case heater elements in accordance with an embodiment of the invention.

In another embodiment, a cast heater plate may be used as shown in FIG. 9. The heater plate 908 may be made to have a very uniform surface temperature by casting heater elements 912 within an aluminum disc 910. In both cases the heater may be constructed with multiple independent zones. Each zone may then be electrically coupled to a controller that will independently switch the current and may also change the current level to each zone independently with such resistive heating elements the heat output may be controlled by changing the amplitude or by pulse width modulation depending on the nature of the controller and the testing plan.

For the example of FIG. 8, a few heater filaments may be grouped together and the heating duty cycle of each group may be controlled individually. In the cast heater of FIG. 9, the heater elements 912 are in the form of concentric rings which may each be controlled individually. A multi-zone heater approach allows careful control of the radial temperature of the Heater and would permit tuning of the radiation heat load to either uniform or non-uniform radial profiles as needed. As an example the inner heater elements might be driven to a higher temperature than the outer heater elements in order to compensate for the lack of heating in the middle of the heater. In another situation there may be hot or cool spots at certain radial distances from the center of the heater due to the shape of the shape of the vacuum chamber or the design of the shutters.

In use, the vacuum chamber may be used for thermal testing of the chuck in a variety of different ways. In one example, the chuck is loaded into the chamber at room temperature and ambient pressure. The chamber is evacuated using a vacuum pump. After or during evacuation, the heater is activated. This causes the chuck to be heated by thermal radiation. After the chamber is evacuated and the interior of the chamber is primarily a vacuum, the heater continues to heat the chuck. At the same time, while the chuck is heating the temperature of the chuck is measured by thermal imaging. During a test, a thermal load can be applied in a quick on-off cycle by opening and closing the shutters. This may be done to mimic the thermal conditions found in an etch process chamber. The camera may then observe changes in the surface temperature of the chuck during the thermal cycling. This test capability provides dramatic improvements in ESC design and manufacturing.

Figure 10:
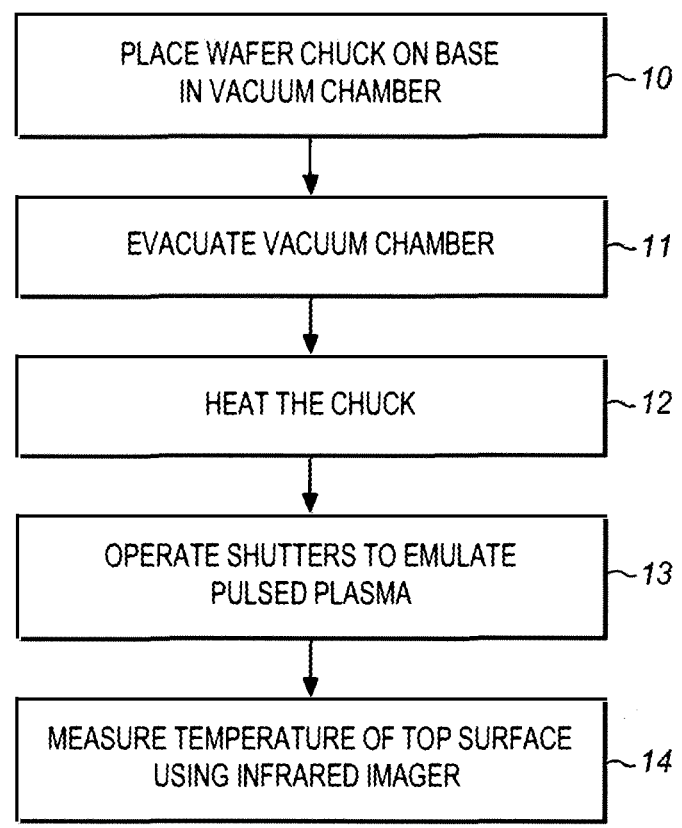
FIG. 10 is a process flow diagram of measuring the thermal performance of a chuck in accordance with an embodiment of the invention.

FIG. 10 is a process flow diagram illustrating a simplified set of operations to evaluate the thermal performance of a chuck using the apparatus described herein. At 10 a wafer chuck, such as but not necessarily an electrostatic chuck, is placed on a base in a vacuum chamber. The wafer chuck has a top surface to hold a wafer. In some cases, a wafer may be attached to the chuck using electrostatic of differential vacuum. The chuck may also be coupled to heat exchangers and power supplies for its heating and cooling system, if it has any.

At 11, the vacuum chamber is evacuated. A special process gas may be introduced, depending on the particular test, or a simple vacuum may be used.

At 12, a heater is activated to heat the chuck. The heater may be activated before the chamber is evacuated by the vacuum pump, or if the heating is slow, the heating may be started before the chamber is completely evacuated. For accurate thermal imaging, a vacuum will eliminate convective heat transfer. Accordingly, chuck performance is better evaluated with the vacuum. The heater may heat the chuck to a temperature of a plasma etch chamber to allow the performance of the chuck to be evaluated at working temperatures.

At 13, shutters are operated between the heater and the chuck. The shutters restrict the flow of heat from the heater to the chuck. When the shutters are closed, heat flow is restricted. When the shutters are open heat flow is unrestricted or less restricted. The shutters are operated during the measuring of the chuck temperature to simulate pulsing of a heat source in a plasma etch chamber.

At 14, the temperature of the top surface of the chuck is measured using an infrared imager outside the vacuum chamber. While these operations are shown as being sequential, they may overlap. As an example, the temperature may be measured while the heater is operating, and the shutters are operating.

The chuck may be heated using an annular shaped heater with multiple different independently controllable heat zones. The heat zones may be concentric about the annulus or in any other configuration depending on the particular test. The heat produced by each of the heat zones can be independently adjusted to mimic a particular plasma condition, perform stress tests, uniformity tests, and even calibration tests.

It is to be understood that the above description is intended to be illustrative, and not restrictive. For example, while flow diagrams in the figures show a particular order of operations performed by certain embodiments of the invention, it should be understood that such order is not required (e.g., alternative embodiments may perform the operations in a different order, combine certain operations, overlap certain operations, etc.). Furthermore, many other embodiments will be apparent to those of skill in the art upon reading and understanding the above description. Although the present invention has been described with reference to specific exemplary embodiments, it will be recognized that the invention is not limited to the embodiments described, but can be practiced with modification and alteration within the spirit and scope of the appended claims. The scope of the invention should, therefore, be determined with reference to the appended claims, along with the full scope of equivalents to which such claims are entitled.

What is claimed is:

1. A method comprising:
   placing a wafer chuck on a base in a vacuum chamber, the wafer chuck having a top surface to hold a wafer;
   evacuating the vacuum chamber;
   heating the chuck; and
   measuring the temperature of the top surface using an infrared imager outside the vacuum chamber.

2. The method of claim 1, wherein heating the chuck comprises heating the chuck to a temperature of a plasma etch chamber.

3. The method of claim 1, further comprising operating shutters between the heater and the chuck during measuring the temperature to simulate pulsing of a heat source in a plasma etch chamber.

4. The method of claim 1, further comprising attaching a wafer to the top surface of the wafer chuck before placing the wafer chuck on the base.

5. The method of claim 1, wherein heating the chuck comprises heating the chuck using radiant heat after evacuating the vacuum chamber.

6. The method of claim 5, wherein heating the chuck comprises heating the chuck with an annular shaped heater with a plurality of independently controllable heat zones.

7. The method of claim 1, wherein measuring the temperature comprises imaging a thermal profile to the top surface of the chuck, the method further comprising independently adjusting the heat radiated by the heat zones of the heater based on the thermal profile.

* * * * *